US008268299B2

(12) United States Patent
Kabra et al.

(10) Patent No.: US 8,268,299 B2
(45) Date of Patent: Sep. 18, 2012

(54) SELF PRESERVED AQUEOUS PHARMACEUTICAL COMPOSITIONS

(75) Inventors: Bhagwati P. Kabra, Euless, TX (US); Masood A. Chowhan, Arlington, TX (US); L. Wayne Schneider, Crowley, TX (US); Wesley Wehsin Han, Arlington, TX (US)

(73) Assignee: Alcon Research, Ltd., Fort Worth, TX (US)

( * ) Notice: Subject to any disclaimer, the term of this patent is extended or adjusted under 35 U.S.C. 154(b) by 754 days.

(21) Appl. No.: 11/858,781

(22) Filed: Sep. 20, 2007

(65) Prior Publication Data
US 2008/0075790 A1 Mar. 27, 2008

Related U.S. Application Data (60) Provisional application No. 60/827,411, filed on Sep. 28, 2006, provisional application No. 60/826,529, filed on Sep. 21, 2006.

(51) Int. Cl.
*A61K 31/74* (2006.01)
*A61K 33/32* (2006.01)
*A61K 33/22* (2006.01)
*A01N 25/00* (2006.01)
*A01N 59/16* (2006.01)
*A01N 59/14* (2006.01)

(52) U.S. Cl. ............... 424/78.04; 424/405; 424/641; 424/657; 424/659; 424/660; 514/912

(58) Field of Classification Search .................. None
See application file for complete search history.

(56) References Cited

U.S. PATENT DOCUMENTS

| | | | |
|---|---|---|---|
| 4,522,806 A | 6/1985 | Muhlemann et al. | |
| 5,130,298 A | 7/1992 | Cini et al. | |
| 5,221,664 A | 6/1993 | Berkowitz et al. | |
| 5,320,843 A | 6/1994 | Raheja et al. | |
| 5,352,708 A | 10/1994 | Woodward et al. | |
| 5,424,078 A | 6/1995 | Dziabo et al. | |
| 5,460,834 A | 10/1995 | Bhagat | |
| 5,597,559 A | 1/1997 | Olejnik et al. | |
| 5,607,698 A | 3/1997 | Martin et al. | |
| 5,683,993 A | 11/1997 | Tsao | |
| 5,725,887 A | 3/1998 | Martin et al. | |
| 5,736,165 A | 4/1998 | Ripley et al. | |
| 5,741,817 A | 4/1998 | Chowhan et al. | |
| 5,817,277 A | 10/1998 | Mowrey-McKee et al. | |
| 5,820,822 A * | 10/1998 | Kross ............... | 422/37 |
| 5,843,891 A * | 12/1998 | Sherman ............ | 424/456 |
| 5,858,346 A | 1/1999 | Vehige et al. | |
| 5,858,996 A | 1/1999 | Tsao | |
| 6,017,861 A | 1/2000 | Fujiwara et al. | |
| 6,024,954 A | 2/2000 | Park et al. | |
| 6,034,043 A | 3/2000 | Fujiwara et al. | |
| 6,121,315 A | 9/2000 | Nair et al. | |
| 6,143,799 A | 11/2000 | Chowhan et al. | |
| 6,319,464 B1 | 11/2001 | Asgharian | |
| 6,348,190 B1 | 2/2002 | Illes et al. | |
| 6,482,799 B1 | 11/2002 | Tuse et al. | |
| 6,492,361 B1 | 12/2002 | Muller et al. | |
| 6,503,497 B2 | 1/2003 | Chowhan et al. | |
| 6,583,124 B2 | 6/2003 | Asgharian | |
| 7,074,827 B2 | 7/2006 | Ueno | |
| 7,445,771 B2 | 11/2008 | Dassanayake et al. | |
| 2002/0098160 A1 | 7/2002 | Chowhan et al. | |
| 2002/0122831 A1 | 9/2002 | Mowrey-McKee et al. | |
| 2002/0123482 A1 * | 9/2002 | Chowhan et al. ........... | 514/59 |
| 2005/0129771 A1 | 6/2005 | Asgharian | |
| 2005/0214382 A1 | 9/2005 | Xia et al. | |
| 2006/0205725 A1 | 9/2006 | Ueno | |
| 2006/0270735 A1 * | 11/2006 | Deaciuc et al. ............ | 514/530 |
| 2007/0212420 A1 | 9/2007 | Xia et al. | |
| 2007/0297990 A1 | 12/2007 | Shah et al. | |
| 2010/0227003 A1 | 9/2010 | Shah et al. | |

FOREIGN PATENT DOCUMENTS

| | | |
|---|---|---|
| JP | 2003-104870 | 9/2001 |
| WO | 95/13050 | 5/1995 |
| WO | 98/10773 | 3/1998 |
| WO | 2005/097067 | 10/2005 |
| WO | 2007/106723 | 9/2007 |
| WO | 2008/036847 | 3/2008 |

OTHER PUBLICATIONS

Bruce et al., Apr. 2001, "Zinc and the eye", Journal Of The American College of Nutrition, 106-118.
Kabara et al., 1997, Preservative-Free and Self-Preserving Cosmetics and Drugs—Principles and Practice, Chapter 1, pp. 1-14, Marcel Dekker, Inc.
McCarthy et al., 1989, "The Effect of Zinc Ions on the Antimicrobial Activity of Selected Preservatives", Journal of Pharmacy and Pharmacology, vol. 41, 114P.
McCarthy, 1985, "Metal Ions as Microbial Inhibitors", Cosmetic & Toiletries, 100:69-72.
PCT International Search Report for corresponding International Application No. PCT/US2007/079082 with mailing date Apr. 7, 2008.

(Continued)

*Primary Examiner* — Ernst V Arnold
(74) *Attorney, Agent, or Firm* — Scott A. Chapple (57) ABSTRACT

The present invention is directed to the provision of multi-dose, self-preserved ophthalmic compositions. The compositions possess sufficient antimicrobial activity to satisfy USP preservative efficacy requirements, as well as similar preservative standards (e.g., EP and JP), without requiring the presence of conventional anti-microbial preservative agents, such as benzalkonium chloride. The compositions are effectively preserved by a balanced ionic buffer system containing zinc ions at a concentration of 0.04 to 0.9 mM, preferably 0.04 to 0.4 mM. One aspect of the balanced buffer system is limitation of the amount of buffering anions present to a concentration of 15 mM or less, preferably 5 mM or less. In a preferred embodiment, the compositions also contain borate or, most preferably, one or more borate/polyol complexes. The use of propylene glycol as the polyol in such complexes is strongly preferred. Limiting the amount of divalent metals other than zinc and the amount of ionized salts present has also been determined to be important to maximize the antimicrobial activity of the balanced buffer systems.

28 Claims, 3 Drawing Sheets

OTHER PUBLICATIONS

PCT Written Opinion for corresponding International Application No. PCT/US2007/079082 with mailing date Apr. 7, 2008, Zeelie et al., 1992, "The Effects of Selected Metal Salts on the Microbial Activities of Agents used in the Pharmaceutical and Related Industries", Metal Compounds in Environment and Life, 4:193-200.

Zeelie et al., 1998, "Effects of copper and zinc ions on the germicidal properties of two popular pharmaceutical antiseptic agents cetylpyridinium chloride and povidone-iodine", Analyst, 123:503-507.

U.S. Appl. No. 12/441,995 Office Action dated Sep. 16, 2011.

U.S. Appl. No. 12/441,742 Office Action dated Jul. 28, 2011.

Guttman, "Liquid gel therapy broadens role of dry eye product line", Ophthalmologytimes.com, 2006, pp. 33-34 and copyright notice.

Hoffman H.M. et al., "Pre-clinical in vitro Testing of an Artificial Tear Formulation with a Novel Preservation System", poster presentation at the annual meeting of the Association for Research In Vision And Opthalmology (ARVO), Ft. Lauderdale, FL, Apr. 30, 2006.

Illustration of packaging for Systane® Free, Mar. 7, 2006.

Systane® Free promotional document (minimal-blur) published on or about Jan. 1, 2006.

* cited by examiner

SELF PRESERVED AQUEOUS PHARMACEUTICAL COMPOSITIONS

CROSS-REFERENCE TO RELATED APPLICATIONS

The present application claims priority based on U.S. Provisional Patent Application Ser. Nos. 60/827,411 filed Sep. 28, 2006, and 60/826,529, filed Sep. 21, 2006.

BACKGROUND OF THE INVENTION

The present invention is directed to self-preserved pharmaceutical compositions. More specifically, the invention is directed to the provision of aqueous, multi-dose pharmaceutical compositions that have been formulated so as to have sufficient antimicrobial activity to satisfy the preservation efficacy requirements of the United States Pharmacopeia ("USP") and analogous guidelines in other countries, without requiring a conventional antimicrobial preservative, such as benzalkonium chloride, polyquaternium-1, hydrogen peroxide (e.g., sodium perborate), or chorine-containing agents. The ability to achieve self-preservation is based on a unique combination of formulation components and criteria.

Many pharmaceutical compositions are required to be sterile (i.e., free of bacteria, fungi and other pathogenic microorganisms). Examples of such compositions include: solutions and suspensions that are injected into the bodies of humans or other mammals; creams, lotions, solutions or other preparations that are topically applied to wounds, abrasions, burns, rashes, surgical incisions, or other conditions where the skin is not intact; and various types of compositions that are applied either directly to the eye (e.g., artificial tears, irrigating solutions, and drug products), or are applied to devices that will come into contact with the eye (e.g., contact lenses).

The foregoing types of compositions can be manufactured under sterile conditions via procedures that are well known to those skilled in the art. However, once the packaging for a product is opened, such that the composition contained therein is exposed to the atmosphere and other sources of potential microbial contamination (e.g., the hands of a human patient), the sterility of the product may be compromised. Such products are typically utilized multiple times by the patient, and are therefore frequently referred to as being of a "multi-dose" nature.

Due to the frequent, repeated exposure of multi-dose products to the risk of microbial contamination, it is necessary to employ a means for preventing such contamination from occurring. The means employed may be: (i) a chemical agent that prevents the proliferation of microbes in a composition, which is referred to herein as an "antimicrobial preservative"; or (ii) a packaging system that prevents or reduces the risk of microbes reaching a pharmaceutical composition within a container.

Prior multi-dose ophthalmic compositions have generally contained one or more antimicrobial preservatives in order to prevent the proliferation of bacteria, fungi and other microbes. Such compositions may come into contact with the cornea either directly or indirectly. The cornea is particularly sensitive to exogenous chemical agents. Consequently, in order to minimize the potential for harmful effects on the cornea, it is preferable to use anti-microbial preservatives that are relatively non-toxic to the cornea, and to use such preservatives at the lowest possible concentrations (i.e., the minimum amounts required in order to perform their anti-microbial functions).

Balancing the anti-microbial efficacy and potential toxicological effects of anti-microbial preservatives is sometimes difficult to achieve. More specifically, the concentration of an antimicrobial agent necessary for the preservation of ophthalmic formulations from microbial contamination may create the potential for toxicological effects on the cornea and/or other ophthalmic tissues. Using lower concentrations of the anti-microbial agents generally helps to reduce the potential for such toxicological effects, but the lower concentrations may be insufficient to achieve the required level of biocidal efficacy (i.e., antimicrobial preservation).

The use of an inadequate level of antimicrobial preservation may create the potential for microbial contamination of the compositions and ophthalmic infections resulting from such contaminations. This is also a serious problem, since ophthalmic infections involving *Pseudomonas aeruginosa* or other virulent microorganisms can lead to loss of visual function or even loss of the eye.

Thus, there is a need for a means of enhancing the activity of anti-microbial agents so that very low concentrations of the agents can be utilized without increasing the potential for toxicological effects or subjecting patients to unacceptable risks of microbial contamination and resulting ophthalmic infections.

Ophthalmic compositions are generally formulated as isotonic, buffered solutions. One approach to enhancing the anti-microbial activity of such compositions is to include multi-functional components in the compositions. In addition to performing their primary functions, these multi-functional components also serve to enhance the overall anti-microbial activity of the compositions.

The following publications may be referred to for further background regarding the use of multi-functional components to enhance the antimicrobial activity of ophthalmic compositions:

1. U.S. Pat. No. 5,817,277 (Mowrey-McKee, et al; tromethamine);
2. U.S. Pat. No. 6,503,497 (Chowhan, et al.; borate/polyol complexes);
3. U.S. Pat. No. 5,741,817 (Chowhan, et al.; low molecular weight amino acids such as glycine);
4. U.S. Pat. No. 6,319,464 (Asgharian; low molecular weight amino alcohols);
5. U.S. Patent Application Publication No. US 2002/0122831 A1 (Mowrey-McKee, et al.; bis-aminopolyols);
6. U.S. Pat. No. 6,348,190 (Illes, et al.; zinc); and
7. JP 2003-104870 (zinc).

The use of zinc to enhance the antimicrobial activity of pharmaceutical compositions, including ophthalmic solutions, is well known. See, for example, the following articles and patent publications, as well as U.S. Pat. No. 6,348,190 and JP 2003-104870, cited above:

McCarthy, "Metal Ions and Microbial Inhibitors", *Cosmetic & Toiletries,* 100:69-72 (February 1985);

Zeelie, et al., "The Effects of Selected Metal Salts on the Microbial Activities of Agents used in the Pharmaceutical and Related Industries", *Metal Compounds in Environment and Life,* 4:193-200 (1992);

Zeelie, et al., "Effects of Copper and Zinc Ions on the Germicidal Properties of Two Popular Pharmaceutical Antiseptic Agents, Cetylpyridinium Chloride and Povidone-iodine", *Analyst,* 123:503-507 (March 1998);

McCarthy, et al., "The Effect of Zinc Ions on the Antimicrobial Activity of Selected Preservatives", *Journal of Pharmacy and Pharmacology,* Vol. 41 (1989);

U.S. Pat. No. 6,482,799 (Tuśe, et al.);
U.S. Pat. No. 5,320,843 (Raheja, et al.);
U.S. Pat. No. 5,221,664 (Berkowitz, et al.);
U.S. Pat. No. 6,034,043 (Fujiwara, et al.);
U.S. Pat. No. 4,522,806 (Muhlemann, et al.);
U.S. Pat. No. 6,017,861 (Fujiwara, et al.); and
U.S. Pat. No. 6,121,315 (Nair, et al.).

The present invention is directed to the provision of improved preservative systems containing zinc ions.

The compositions of the present invention are multi-dose products that do not require a conventional antimicrobial preservative (e.g., benzalkonium chloride), and yet are preserved from microbial contamination. Such compositions have been referred to in the art as being "preservative free" (see, e.g., U.S. Pat. No. 5,597,559 issued to Olejnik, et al.). Compositions that are preserved from microbial contamination as a result of the inherent antimicrobial activity of one or more components of the compositions are also referred to in the art as being "self-preserved" (see, e.g., U.S. Pat. No. 6,492,361 issued to Muller, et al.).

The following publication may be referred to for further background regarding pharmaceutical compositions that are "preservative-free" or "self-preserving": Kabara, et al., *Preservative-Free and Self-Preserving Cosmetics and Drugs—Principles and Practice*, Chapter 1, pages 1-14, Marcel Dekker, Inc. (1997).

The multi-dose compositions of the present invention, which do not contain a conventional antimicrobial preservative, are referred to herein as being "self-preserved".

SUMMARY OF THE INVENTION

The present invention is directed to the self-preservation of aqueous ophthalmic compositions via the use of very low concentration of zinc ions. The present invention is based in part on the finding that in order to utilize low concentrations of zinc ions to self-preserve multi-dose ophthalmic compositions having ophthalmically acceptable pH and osmolality values, certain formulation parameters must be maintained. Specifically, the concentration of buffering anions utilized to maintain the pH within an ophthalmically acceptable range must be limited to an amount of 15 millimolar ("mM") or less in order to avoid interfering with the anti-microbial activity of the zinc ions.

In addition, it has been determined that the antimicrobial activity of the zinc-containing compositions of the present invention can be further enhanced by the use of zinc ions in combination with borate or a borate/polyol complex, and that if such a combination is utilized, the use of propylene glycol is strongly preferred, so as to avoid ionic interactions between anionic species generated by other polyols (e.g., sorbitol) and the zinc cations.

It has also been determined that the performance of the zinc-based preservative systems of the present invention is further enhanced by: (i) limiting the amount of multivalent metal cations other than zinc (e.g., calcium and magnesium) in the compositions of the present invention; and (ii) limiting the amount of ionized salts (e.g., sodium chloride and potassium chloride) in said compositions. As described in greater detail below, the compositions of the present invention are preferably free of or substantially free of both ionized salts and multivalent metal cations other than zinc.

The self-preserved, multi-dose compositions of the present invention have several advantages over existing ophthalmic formulations that are either: (i) packaged as a "single dose" or "unit of use" product, so as to avoid the inclusion of any antimicrobial preservative (e.g., BION®TEARS Lubricant Eye Drops, which is marketed by Alcon Laboratories, Inc.), or (ii) preserved by means of a so-called "disappearing" preservatives, such as the chlorite-based system described in U.S. Pat. Nos. 5,424,078; 5,736,165; 6,024,954; and 5,858, 346 (e.g., the artificial tears product "REFRESH™ Tears", which is marketed by Allergan), or the peroxide-containing system described in U.S. Pat. Nos. 5,607,698; 5,683,993; 5,725,887; and 5,858,996 (e.g., the artificial tear product "GenTeal™ Tears", which is marketed by CIBA Vision).

Unlike these existing products, the multi-dose ophthalmic compositions of the present invention are able to satisfy the USP preservative efficacy requirements, as well as analogous requirements in other countries, including the Japanese Pharmacopoeia ("JP") and European Pharmacopoeia ("EP") preservative efficacy standards, without employing any conventional antimicrobial preservatives, such as chlorite or hydrogen peroxide.

The above-discussed findings regarding the zinc may be applied to enhance the antimicrobial activity of various types of pharmaceutical compositions. However, the present invention is particularly directed to the provision of aqueous ophthalmic solutions that are effective in preventing microbial contamination in the absence of conventional antimicrobial preservatives, such as benzalkonium chloride ("BAC"), polyquaternium-1, chlorite or hydrogen peroxide.

DETAILED DESCRIPTION OF THE INVENTION

The pharmaceutical compositions of the present invention contain zinc ions at a concentration of 0.04 to 0.9 millimoles/liter ("mM"), preferably 0.04 to 0.4 mM and most preferably 0.1 to 0.4 mM. The use of this very low concentration is particularly desirable in ophthalmic pharmaceutical compositions containing therapeutically active agents, such as prostaglandin analogues used to control intraocular pressure (e.g., travoprost), because at higher concentrations the zinc ions may produce an astringent effect when applied to the eye. The zinc ions are preferably provided in the form of zinc chloride, at a concentration of 0.0005 to 0.012 percent by weight/volume ("w/v %"), preferably 0.0005 to 0.005 w/v % and most preferably 0.001 to 0.005 w/v %.

The zinc may be provided in various forms, such as zinc chloride, zinc sulfate, zinc acetate or zinc carbonate. The use of zinc chloride is preferred.

As indicated above, the present invention is based on part on a finding that anionic agents utilized to buffer the compositions of the present invention may interfere with the ability of zinc to exert antimicrobial activity. Such interference can be very detrimental to the ability of the compositions to maintain sufficient antimicrobial activity to meet preservative efficacy standards, particularly in view of the very low concentrations of zinc utilized in the present invention. Accordingly, it has been determined that the total concentration of anionic species in the compositions of the present invention should be limited. Specifically, it is preferred that the total concentration of anionic species, particularly buffering anions, should be limited to an amount of less than 15 mM, more preferably less than 10 mM, and most preferably less than 5 mM. For simplicity and clarity, the concentration of buffering anionic species in this patent application will be represented by the concentration of monovalent cations (such as sodium) that are present or needed to bring the pH to the specified value.

As utilized herein, the phrase "less than" relative to a specified concentration (e.g., 15 mM) means that the specified component (e.g., buffering anions) is either not present in the composition at all or is present at a concentration less than the specified limit (e.g., 15 mM).

It has been determined that multivalent buffering anions, particularly citrate and phosphate, have a significant adverse effect on the antimicrobial activity of the zinc-based preservative systems described herein. The compositions of the present invention therefore preferably do not contain any multivalent buffering anions, other than borate-polyol complexes, which may be multivalent under certain conditions (e.g., pH and/or borate:polyol ratio), or are substantially free of such buffering anions. As utilized herein, the phrase "substantially free of multivalent buffering anions" means that the composition either does not contain any multivalent buffering anions or contains an amount of said anions that does not inhibit the ability of the composition to satisfy specified preservative efficacy standards (e.g., USP, EP or JP). The amount of multivalent buffering anions in the compositions of the present invention is preferably less than 5 mM, with said concentration being determined in the same manner as specified in the preceding paragraph.

As indicated above, it has been determined that the antimicrobial activity of the zinc-based preservative systems of the present invention is also adversely affected by other divalent cations, such as calcium and magnesium. The antimicrobial activity of divalent zinc ions ($Zn^{2+}$) is based upon the ability of the ions to competitively bind and inactivate macromolecular complexes that are critical to the central metabolic activity of the prokaryotic cell. In order for Zn to kill, it must first gain access to the cytoplasm and its charge density prevents its diffusion across the membrane at a physiologically significant rate. Therefore, the ability of $Zn^{2+}$ ions to enter the cell must be facilitated by membrane transport proteins. Access to these transport proteins can be competitively inhibited by multivalent metal cations, particularly $Mg^{2+}$, $Ca^{2+}$, $Mn^{2+}$, $Ni^{2+}$, and $Co^{2+}$. Thus, increasing the extracellular concentration of these inhibitory cations diminishes the capacity of $Zn^{2+}$ ions to gain access to the cytoplasm and subsequently reduces its cytotoxic activity to the microorganism.

In view of the potential interference of multivalent metal cations other than zinc, the compositions of the present invention preferably do not contain such cations or are substantially free of said cations. As utilized herein, the phrase "substantially free of multivalent metal cations other than zinc" means that the composition either does not contain such cations or contains an amount of said cations that does not inhibit the ability of the composition to satisfy specified preservative efficacy standards (e.g., USP, EP or JP). The amount of multivalent metal cations other than zinc in the compositions of the present invention is preferably less than 5 mM.

It has also been determined that ionized salts (e.g., sodium chloride and potassium chloride) adversely affect the antimicrobial activity of the preservative systems described herein. Accordingly, the compositions of the present invention preferably do not contain ionized salts, or are substantially free of ionized salts. As utilized herein, the phrase "substantially free of ionized salts" means that the composition either does not contain any ionized salt or contains an amount of ionized salt that does not inhibit the ability of the composition to satisfy specified efficacy standards (e.g., USP, JP or EP). The amount of ionized salt contained in the compositions of the present invention is preferably less than 50 mM.

As used herein, the term "borate" includes boric acid, sodium borate and potassium borate. The use of borates containing divalent cations (e.g., calcium borate) may adversely affect the antimicrobial action of zinc ions, by competing with zinc for binding sites on the cell walls of bacterial and other microbes, and is therefore should be avoided. For the same reason, the self-preserved compositions of the present invention are preferably free of or substantially free of other sources of divalent cations, such as calcium chloride.

The self-preserved compositions of the present invention preferably contain one or more borates in an amount of from about 0.1 to about 2.0% w/v, more preferably 0.3 to 1.5% w/v, and most preferably 0.5 to 1.2% w/v.

As used herein, the term "polyol" includes any compound having at least one hydroxyl group on each of two adjacent carbon atoms that are not in trans configuration relative to each other. The polyols can be linear or cyclic, substituted or unsubstituted, or mixtures thereof, so long as the resultant complex is water soluble and pharmaceutically acceptable. Examples of such compounds include: sugars, sugar alcohols, sugar acids and uronic acids. Preferred polyols are sugars, sugar alcohols and sugar acids, including, but not limited to: mannitol, glycerin, xylitol, sorbitol and propylene glycol.

As indicated above, the use of propylene glycol is particularly preferred in order to limit the presence of anionic species. Boric acid interacts with polyols, such as glycerol, propylene glycol, sorbitol and mannitol, to form borate polyol complexes. The type and ratio of such complexes depends on the number of OH groups of a polyol on adjacent carbon atoms that are not in trans configuration relative to each other. For example, propylene glycol has only one OH group on each of two adjacent carbon atoms that are not in trans configuration. Consequently, one molecule of boric acid will interact and form a complex with one or two molecules of propylene glycol, resulting in a monovalent anion. However, in the case of sorbitol, mannitol and other sugar-type polyols, this interaction is much more complex, because one molecule of such polyols can complex with two molecules of borate and then further complex with two additional molecules of the polyol, resulting in a multivalent anion.

When borate is present in the compositions of the present invention, the compositions preferably also contain one or more polyols, at a total concentration of 0.25 to 2.5% w/v. The polyol preferably is propylene glycol at a concentration of 0.25 to 1.80% w/v, preferably 0.25 to 1.25% w/v. Although less preferable than propylene glycol, sorbitol and mannitol are also preferred polyols, and preferably are used at a concentration of 0.05 to 0.75% w/v, preferably 0.05 to 0.5% w/v.

The compositions of the present invention preferably contain borate or a borate/polyol complex, most preferably a borate/polyol complex wherein the polyol portion of the complex is propylene glycol or a combination of propylene glycol and sorbitol. The preference for propylene glycol is based on a discovery that sorbitol and other polyols have a greater tendency to form anionic species at pH values of 7.5 or less, and that such anionic species may interfere with the antimicrobial activity of zinc. The graphs shown in FIGS. 1-3 demonstrate that sorbitol has a much higher tendency to form anionic species in the presence of boric acid, compared to propylene glycol.

Figure 1:
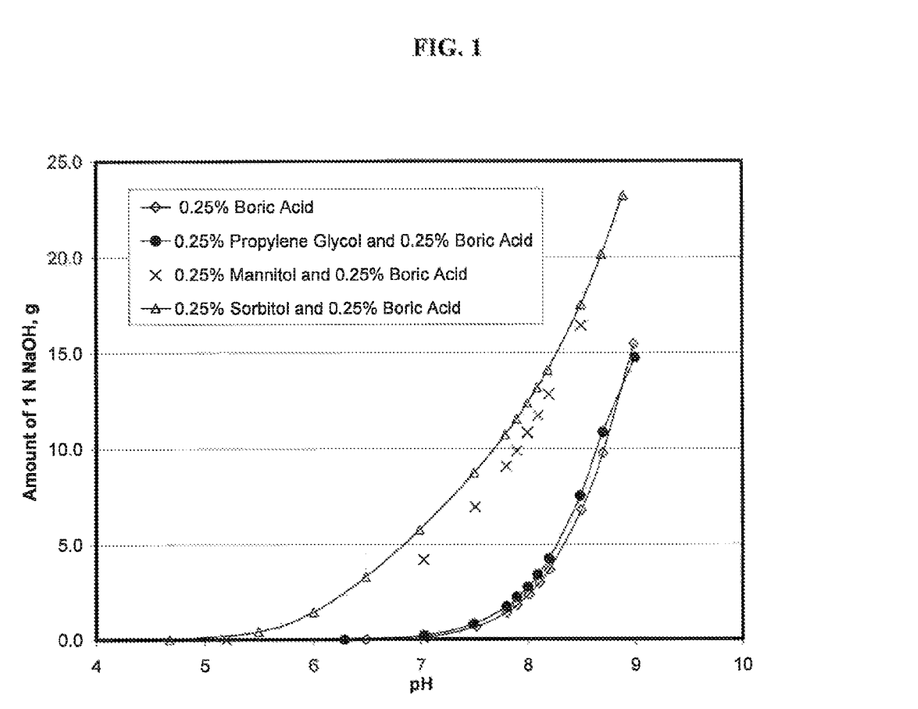
FIG. 1 is a graph showing the amount of 1 N Sodium Hydroxide needed to adjust pH of 1 Kg solution of Boric Acid (0.25%) in presence of mannitol, sorbitol or propylene glycol.
Figure 2:
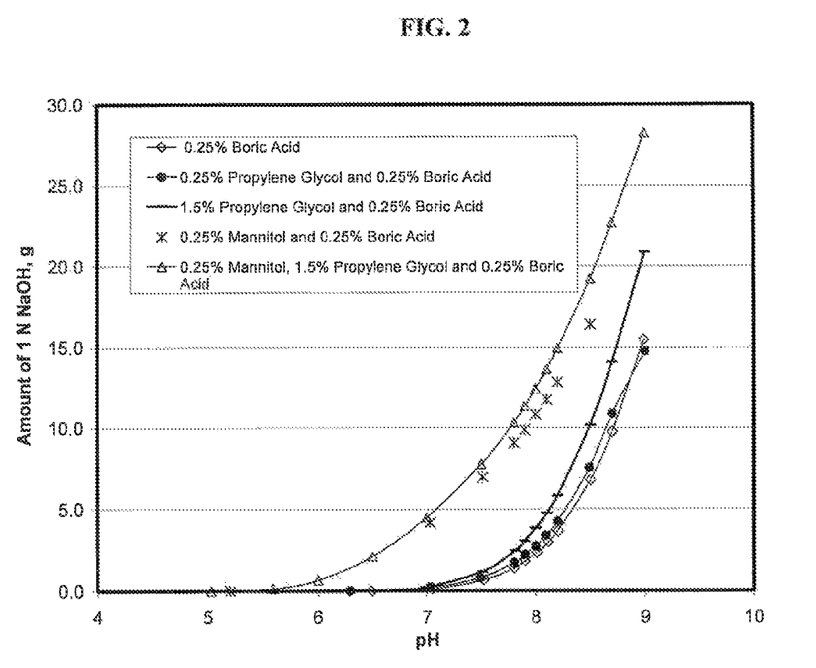
FIG. 2 is a graph showing the amount of 1 N Sodium Hydroxide needed to adjust pH of 1 Kg solution of Boric Acid (0.25%) in presence of propylene glycol.
Figure 3:
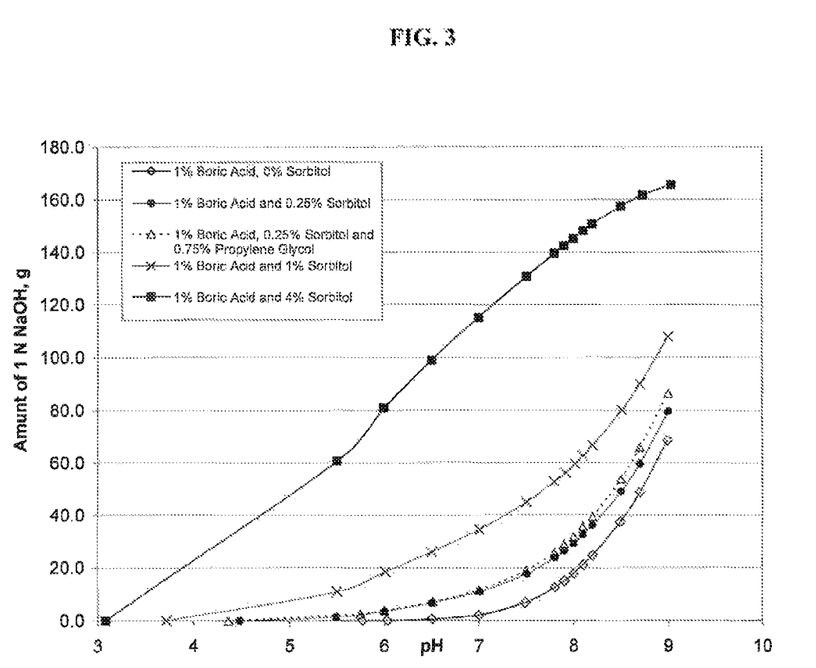
FIG. 3 is a graph showing the amount of 1 N Sodium Hydroxide needed to adjust pH of 1 Kg solution Boric Acid (1%) in presence of different concentrations of sorbitol.

The data shown in FIGS. 1-3 were compiled as follows: A 1 Kg solution containing the given concentrations of boric acid and propylene glycol or sorbitol or mannitol was prepared and the initial pH of the solution was determined. 1 N NaOH was then added to adjust the pH. The cumulative amount of sodium hydroxide used to adjust pH to different values was then recorded.

As explained above, boric acid interacts and forms an ionic complex with species containing several hydroxyl groups, such as mannitol and sorbitol. However, the interaction between boric acid and propylene glycol is more limited than with other polyols. This is represented by the amount of sodium hydroxide needed to adjust pH, as shown in FIG. 1. Sorbitol and mannitol significantly shift the curve relative to the amount of NaOH required to lower pH, whereas propylene glycol only slightly shifts the curve. This is further evident in FIG. 2.

The present invention is particularly directed to the provision of multi-dose, self-preserved ophthalmic compositions that have sufficient antimicrobial activity to allow the compositions to satisfy the USP preservative efficacy requirements, as well as other preservative efficacy standards for aqueous pharmaceutical compositions, without a conventional antimicrobial preservative.

The preservative efficacy standards for multi-dose ophthalmic solutions in the U.S. and other countries/regions are set forth in the following table:

| | Preservative Efficacy Test ("PET") Criteria (Log Order Reduction of Microbial Inoculum Over Time | |
|---|---|---|
| | Bacteria | Fungi |
| USP 27 | A reduction of 1 log (90%), by day 7; 3 logs (99.9%) by day 14; and no increase after day 14 | The compositions must demonstrate over the entire test period, which means no increases of 0.5 logs or greater, relative to the initial inoculum. |
| Japan | 3 logs by 14 days; and no increase from day 14 through day 28. | No increase from initial count at 14 and 28 days |
| Ph. Eur. A[1] | A reduction of 2 logs (99%) by 6 hours; 3 logs by 24 hours; and no recovery after 28 days | A reduction of 2 logs (99%) by 7 days, and no increase thereafter |
| Ph. Eur. B | A reduction of 1 log at 24 hours; 3 logs by day 7; and no increase thereafter | A reduction of 1 log (90%) by day 14, and no increase thereafter |
| FDA/ISO 14730 | A reduction of 3 logs from initial challenge at day 14; and a reduction of 3 logs from rechallenge | No increase higher than the initial value at day 14, and no increase higher than the day 14 rechallenge count through day 28. |

[1]There are two preservative efficacy standards in the European Pharmacopoeia ' "A" and "B".

The standards identified above for the USP 27 are substantially identical to the requirements set forth in prior editions of the USP, particularly USP 24, USP 25 and USP 26.

The compositions of the present invention may optionally also include one or more low molecular weight amino alcohols as buffering agents. The amino alcohols which may be utilized in the present invention are water-soluble and have a molecular weight in the range of from about 60 to about 200. The following compounds are representative of the low molecular weight amino alcohols which may be utilized in the present invention: 2-amino-2-methyl-1-propanol (AMP), 2-dimethylamino-methyl-1-propanol (DMAMP), 2-amino-2-ethyl-1,3-propanediol (AEPD), 2-amino-2-methyl-1,3-propanediol (AMPD), 2-amino-1-butanol (AB). "AMP (95%)", which refers to 95% pure AMP and 5% water, is the most preferred low molecular weight amino alcohol of the present invention. These amino alcohols are available commercially from Angus Chemical Company (Buffalo Grove, Ill.). Tromethamine may also be utilized in the compositions of the present invention.

The amount of amino alcohol used will depend on the molecular weight of the amino alcohol selected, and the presence (or absence) of other ingredients in the composition (e.g., chelating agents, buffering agents and/or tonicity agents). The amino alcohol will generally be present in an amount necessary to enhance the antimicrobial activity of an aqueous self-preserved pharmaceutical composition of the type described herein. The amount of amino alcohol required for a particular composition can be determined through comparative testing. The above-described amino alcohols are also utilized in the compositions of the present invention to neutralize the pH of the borate or borate/polyol complex, or bring the composition to the desired pH level. The amount of amino alcohol required for this purpose is a function of the particular borate or borate/polyol mixture selected and the concentration thereof. In general, the self-preserved compositions of the present invention may optionally contain one or more amino alcohols at a total concentration of from about 0.01 to about 2.0 percent by weight/volume ("% w/v"), and preferably from 0.1 to 1.0% w/v.

The zinc, zinc/borate, zinc/polyol and zinc/borate/polyol systems described herein may be included in various types of pharmaceutical compositions to enhance anti-microbial activity and self-preserve the compositions, such as ophthalmic, otic, nasal and dermatological compositions, but is particularly useful in ophthalmic compositions. Examples of such compositions include: ophthalmic pharmaceutical compositions, such as topical compositions used in the treatment of glaucoma, infections, allergies or inflammation; compositions for treating contact lenses, such as cleaning products and products for enhancing the ocular comfort of patients wearing contact lenses; and various other types of ophthalmic compositions, such as ocular lubricating products, artificial tears, astringents, and so on. The compositions may be aqueous or non-aqueous, but will generally be aqueous.

The compositions of the present invention may contain various types of therapeutic agents. However, the invention is most useful relative to therapeutic agents that are nonionic, since nonionic agents do not interfere with the antimicrobial activity of zinc cations in solution. Cationic therapeutic agents may also be utilized in the compositions, particularly if the agent is included in the compositions in free base form or in the form of a salt with a monovalent anion, such as a hydrochloride salt. Cationic therapeutic agents that are included in the compositions in the form of a salt of a multivalent anion may interfere with the antimicrobial activity of the zinc preservative systems described herein, depending on the concentration of the anion. Such interference must be considered when selecting therapeutic agents that are suitable for use in the compositions of the present invention. Similarly, the use of therapeutic agents that are anionic may be considered; however, such agents may interfere with the activity of zinc ions, depending on the concentration of the agent and its dissociation constant.

Examples of therapeutic agents that may be contained in the ophthalmic compositions of the present invention include prostaglandin analogs (e.g., latanoprost, travoprost and unoprostone), hypotensive lipids (e.g., bimatoprost), and glucocorticoids (e.g., prednisolone, dexamethasone and lotoporednol).

The present invention is particularly directed to the provision of self-preserved, multi-dose ophthalmic compositions in connection with the treatment of conditions wherein the cornea or adjacent ocular tissues are irritated, or conditions requiring frequent application of a composition, such as in the treatment of dry eye patients. The self-preserved compositions of the present invention are therefore particularly useful in the field of artificial tears, ocular lubricants, and other compositions used to treat dry eye conditions, as well as other conditions involving ocular inflammation or discomfort.

The compositions of the present invention will generally be formulated as sterile aqueous solutions. The compositions of the present invention are also formulated so as to be compatible with the eye and/or other tissues to be treated with the compositions. The ophthalmic compositions intended for direct application to the eye will be formulated so as to have a pH and tonicity that are compatible with the eye.

The compositions will have a pH in the range of 4 to 9, preferably 5.5 to 8.5, and most preferably 5.5 to 8.0. It has been determined that a slightly alkaline pH increases the antimicrobial activity of the compositions of the present invention. The use of a pH in the range of 7.0 to 8.0 is therefore preferred.

The compositions will have an osmolality of 200 to 350 milliosmoles per kilogram (mOsm/kg), more preferably 250 to 330 mOsm/kg. As indicated above, the use of nonionic osmolality-adjusting agents is preferred, as ionic salts such as sodium chloride have been found to reduce the antimicrobial activity of the zinc-based preservative systems described herein. The use of propylene glycol, glycerol, xylitol or combinations thereof as nonionic osmolality adjusting agents is particularly preferred. Boric acid may also be utilized as an osmolality-adjusting agent in the compositions of the present invention. Boric acid, if utilized, will be present in the compositions as a mixture of ionic and nonionic species.

The compositions of the present invention may contain various types of pharmaceutical excipients, such as surfactants, viscosity-modifying agents and so on, provided that such excipients are non-ionic. The use of excipients that are cationic or anionic is not preferred, since such ionic agents may interfere with the zinc-based preservation systems described herein. This is particularly true with respect to anionic excipients. Accordingly, the compositions of the present invention are preferably free of or substantially free of anionic excipients.

In the event cationic or anionic excipients are utilized, the amount of excipient contained in the compositions must be limited to an amount that does not inhibit the ability of the composition to meet the applicable preservative efficacy requirements (e.g., USP, JP and/or EP) and adjustments to the formulation properties may be required. For example, the nonionic surfactant polyoxyl 40 hydrogenated castor oil can be used for solubilization or stabilization of drugs, such as travoprost. However, it has been determined that 12-hydroxy stearic acid, an anionic compound that has been determined to be present as an impurity and potential degradation product of the excipient polyoxyl 40 hydrogenated castor oil, interacts with zinc and forms particles. In order to avoid particle formation throughout the commercial shelf-life of a composition containing these components, the pH of the composition needs to be in the range 5.0 to 6.0, preferably in the range 5.5 to 5.9. These finding are further illustrated in Example Y, below.

One or more conventional antimicrobial preservatives (e.g., benzalkonium chloride and polyquaternium-1) can be present in the compositions of the present invention, if desired, but the compositions preferably do not contain any conventional antimicrobial preservatives. If utilized, such preservatives can be present in conventional amounts, but in view of the self-preserving properties of the compositions of the present invention, such conventional antimicrobial preservatives can also be utilized in much lower concentrations than would be required to satisfy preservative efficacy requirements if only the conventional antimicrobial preservative were present. Since the present compositions can be a self-preserved composition, if an anti-microbial preservative is present as an option, the amount can be an amount that would not be effective alone as an antimicrobial preservative agent. However, the overall composition would have sufficient antimicrobial activity to satisfy USP/FDA/ISO preservative efficacy requirements.

Preferably the conventional antimicrobial preservative, if present, is not anionic and if anionic, it is preferred that the amount should be low enough to not substantially interfere with the antimicrobial activity of the preservative systems described herein.

Applicants specifically incorporate the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Other embodiments of the present invention will be apparent to those skilled in the art from consideration of the present specification and practice of the present invention disclosed herein. It is intended that the present specification and examples be considered as exemplary only with a true scope and spirit of the invention being indicated by the following claims and equivalents thereof.

The following examples are presented to further illustrate selected embodiments of the present invention. The formulations shown in the examples were prepared using procedures that are well-known to persons of ordinary skill in the field of ophthalmic pharmaceutical compositions.

Antimicrobial preservative effectiveness as set forth by the examples infra was determined using an organism challenge test according to the methods described in the United States Pharmacopeia 24 (USP) for category 1A products. Samples were inoculated with known levels of one or more of the following: gram-positive vegetative bacteria (*Staphylococcus aureus* ATCC 6538), gram-negative vegetative bacteria (*Pseudomonas aeruginosa* ATCC 9027 and *Escherichia coli* ATCC 8739), yeast (*Candida albicans* ATCC 10231) and mold (*Aspergillus niger* ATCC 16404). The samples were then pulled at specified intervals to determine if the antimicrobial preservative system was capable of killing or inhibiting the propagation of organisms purposely introduced into the formulation. The rate or level of antimicrobial activity determines compliance with the USP preservative efficacy standards for the cited categories of preparations. In some instances, the PET screen test was conducted for only 7 days, rather than 14 or 28 days, with additional time points of 6 and 24 hours being added to evaluate preservative efficacy relative to Ph. Eur. B. criteria. This modified PET screen test has been shown to be a reliable test for determining whether a composition will meet USP or Ph. Eur. B criteria.

TABLE 1

Preservative Standards for U.S. Category 1A Products presented as Log Reduction of Organism Population

| Time Pulls | 24 Hours | 7 days | 14 days | 28 days |
|---|---|---|---|---|
| For Bacteria (*S. aureus*, *P. aeruginosa*, and *E. coli*) | | | | |
| Ph. Eur. B | 1.0 | 3.0 | NI | NI |
| USP | NA | 1.0 | 3.0 | NI |
| For Fungi (*C. albicans* and *A. niger*) | | | | |
| Ph. Eur. B | NA | NA | 1.0 | NI |
| USP | NA | NI | NI | NI |

NI = No increase at this or any following time pulls
NA = Time point not required for applicable standard (e.g., USP or Ph. Eur. B)

As shown in Table 1, the USP 24 Antimicrobial Effectiveness Test requires that compositions containing Category 1A products have sufficient anti-bacterial activity to reduce an initial inoculum of approximately $10^5$ to $10^6$ bacteria by one log (i.e., a 90% reduction in the microorganism population) over a period of seven (7) days and by three logs (i.e., a 99.9% reduction in the microorganism population) over a period of fourteen (14) days, and requires that there cannot be any increase in the microorganism population following the conclusion of the fourteen day period. Relative to fungi, the USP standards require that the compositions maintain stasis (i.e., no growth) relative to the population of the initial inoculum over the entire 28 day test period. A category 1A product is an injection, or other parenteral including emulsions, otic, sterile nasal products and ophthalmic products made with aqueous bases or vehicles.

The margin of error in calculating microorganism populations is generally accepted to be +/−0.5 logs. Accordingly, the term "stasis", as utilized herein relative to the above-discussed USP standards, means that the initial population cannot increase by more than 0.5 log orders, relative to the initial population.

EXAMPLES A-E

The formulations of Examples A-E were evaluated to determine the effect of buffering anions on preservative efficacy. As discussed in greater detail below, the formulations of Examples A and B do not contain buffering agents. Although these formulations satisfied the USP preservative efficacy requirements, the presence of a buffering system is highly desirable, so as to prevent pH drift over the life of a commercial product (i.e., a period of up to two years or more). The formulation of Example C include a borate/polyol buffering system, but the system has minimal buffering capacity. As with the formulations of Examples A and B, the formulation of Example C satisfied the USP requirements. The formulations of Examples D and E contain significantly greater concentrations of buffering agents and consequently a higher buffering capacity. However, the relatively large amount of buffering anions present resulted in a failure of the formulations to satisfy preservative efficacy requirements. Thus, a comparison of Examples A-E demonstrates the need to balance the requirements for an effective buffering system with the antimicrobial activity required to satisfy preservative efficacy requirements.

The formulation of Example A does not have any buffering ingredient. The amount of sodium hydroxide used in the formulation (0.2 mM) to adjust pH is minimal, which means that the buffering anion concentration is very low. This formulation containing 0.18 mM zinc (0.0025% zinc chloride) meets USP preservation criteria, but is not desirable from a commercial perspective due to the lack of buffering capacity.

Though the formulation of Example B contains boric acid, it does not have buffering capacity as the pKa of boric acid (alone) is much higher than 6. The amount of sodium hydroxide used in the formulation (0.3 mM) to adjust pH is minimal. This formulation containing 0.18 mM zinc (0.0025% zinc chloride) meets USP preservation criteria, but is not commercially desirable due to the lack of buffering capacity.

The formulation of Example C includes two excipients, boric acid and propylene glycol, which together add significantly to the osmolality of the composition and provide minimal buffering capacity. The amount of sodium hydroxide required in this formulation to adjust pH (0.5 mM) is somewhat higher than for the formulations of Examples A and B, but still very low compared to the limits specified herein (i.e., less than 15 mM, more preferably less than 5 mM). This formulation, containing 0.18 mM Zinc (0.0025% zinc chloride), meets USP preservation criteria, but the buffering capacity is not ideal relative to commercial viability.

Adding boric acid and sorbitol in the amounts indicated for the formulations of Examples D and E provides significant buffering capacity, but results in very high buffering anion concentrations (i.e., 77 and 49 mM, respectively). Example D does not meet USP preservation criteria for either *S. aureus* or *E. coli* at days 7 and 14. Example E does not meet USP preservation criteria for *S. aureus* at day 14 or for *E. coli* at days 7 and 14. These results demonstrate that the addition of significant amounts of buffering anions disrupted the preservation activity of the compositions. Thus, although the buffering systems of the formulations in Examples D and E are commercially viable, the preservative systems do not satisfy USP requirements and consequently would not be acceptable for a commercial product subject to the USP requirements or similar requirements in countries other than the U.S.

| Example | A | B | C | D | E |
|---|---|---|---|---|---|
| FID | 107339 | 107340 | 107431 | 106737 | 106757 |
| Lot Number | 04-37152 | 04-37160-1 | 04-37290 | 04-36171 | 04-36176 |
| Ingredient | Concentration (w/v %) | | | | |
| Travoprost | 0.004 | 0.004 | 0.004 | 0.004 | 0.004 |
| Polyoxyl 40 Hydrogenated Castor Oil (HCO-40) | 0.5 | 0.5 | 0.5 | 0.5 | 0.5 |
| Zinc Chloride | 0.0025 | 0.0025 | 0.0025 | 0.0025 | 0.0025 |
| Boric Acid | None | 1 | 1 | 1 | 0.5 |
| Sorbitol | 0.25 | None | None | 3.8 | 3.2 |
| Propylene Glycol | 0.75 | None | 0.75 | None | None |
| Sodium Hydroxide, and/or Hydrochloric Acid | Adjust pH to 6.0 | Adjust pH to 6.0 | Adjust pH to 6.0 | Adjust pH to 6.0 | Adjust pH to 6.0 |

-continued

| Example | A | B | C | D | E |
|---|---|---|---|---|---|
| FID | 107339 | 107340 | 107431 | 106737 | 106757 |
| Lot Number | 04-37152 | 04-37160-1 | 04-37290 | 04-36171 | 04-36176 |
| Purified Water | QS 100% | QS 100% | QS 100% | QS 100% | QS 100% |
| Osmolality | 113 | Not tested | 274 | 291 | 208 |
| Monovalent cation (Na) conc. needed to adjust pH of buffering anions | 0.2 mM | 0.3 mM | 0.5 mM | 77 mM | 49 mM |

| Microorganism | Log Order Reductions | | | | |
|---|---|---|---|---|---|
| *S. aureus* | | | | | |
| 7 D | 5.0 | 5.0 | 4.7 | 0.9 | 1.1 |
| 14 D | 5.0 | 5.0 | 4.7 | 1.8 | 2.3 |
| 28 D | 5.0 | 5.0 | 4.7 | 4.4 | 4.7 |
| *P. aeruginosa* | | | | | |
| 7 D | 5.0 | 5.0 | 4.9 | 2.1 | 4.0 |
| 14 D | 5.0 | 5.0 | 4.9 | 4.3 | 4.9 |
| 28 D | 5.0 | 5.0 | 4.9 | 5.1 | 4.9 |
| *E. coli* | | | | | |
| 7 D | 5.0 | 5.0 | 4.5 | 0.9 | 0.9 |
| 14 D | 5.0 | 5.0 | 5.1 | 1.4 | 2.1 |
| 28 D | 5.0 | 5.0 | 5.1 | 5.2 | 4.9 |
| *C. albican* | | | | | |
| 7 D | 1.4 | 0.0 | 0.0 | 0.3 | 0.1 |
| 14 D | 3.3 | 0.6 | 0.2 | 0.4 | 0.6 |
| 28 D | 3.4 | 4.9 | 0.9 | 0.7 | 1.5 |
| *A. niger* | | | | | |
| 7 D | 0.0 | 1.4 | 0.7 | 3.4 | 2.7 |
| 14 D | 0.7 | 2.2 | 0.2 | 3.7 | 3.7 |
| 28 D | 0.6 | 2.3 | 0.5 | 4.9 | 4.3 |

EXAMPLES F THROUGH J

In these examples, the amount of sorbitol was reduced to 1%, while keeping the boric acid concentration at 1%, in order to reduce the concentration of buffering anionic species. In addition, examples G, I, and J contain 0.75% propylene glycol. All five examples have an anionic buffer concentration of about 19 mM.

The compositions of Examples F and G contain 0.18 mM of zinc. These have much better anti-microbial activity against *S. Aureus* than the formulations of Examples D and E, above. Specifically, the compositions of Examples F and G meet USP preservation criteria for *S. aureus*. However, although the antimicrobial activity against *E. coli* at zinc concentrations of 0.18 mM (Examples F and G) and 0.36 mM (Example H and I) is improved, compared to examples D and E, it is not sufficient to consistently meet USP preservation criteria at day 14. Increasing the zinc concentration to 1.8 mM (Example J) improved the antimicrobial activity of the solution, so as to allow it to meet USP criteria. However, as indicated above, such higher concentration of zinc are not preferred in ophthalmic products, as zinc may provide astringent activity at these concentrations.

All of the formulations of Examples F-J contained anionic buffer concentrations of 19 mM, which is greater than the preferred limit of 15 mM specified herein. The fact that these compositions were not able to consistently meet or exceed the USP preservative efficacy requirements, even at relatively high zinc concentrations, further demonstrates the importance of limiting the concentration of buffering anions.

| Example | F | G | H | I | J |
|---|---|---|---|---|---|
| FID | 106039 | 106755 | 107038 | 107039 | 107099 |
| Lot Number | 04-36405 | 04-36173 | 04-36479 | 04-36476 | 04-36632 |
| Ingredient | Concentration (w/v %) | | | | |
| Travoprost | 0.004 | 0.004 | 0.004 | 0.004 | 0.004 |
| Polyoxyl 40 Hydrogenated Castor Oil (HCO-40) | 0.5 | 0.5 | 0.5 | 0.5 | 0.5 |
| Zinc Chloride | 0.0025 | 0.0025 | 0.005 | 0.005 | 0.025 |
| Boric Acid | 1 | 1 | 1 | 1 | 1 |
| Sorbitol | 1 | 1 | 1 | 1 | 1 |
| Propylene Glycol | None | 0.6 | None | 0.6 | 0.6 |
| Sodium Hydroxide, and/or Hydrochloric Acid | Adjust pH to 6.0 | Adjust pH to 6.0 | Adjust pH to 6.0 | Adjust pH to 6.0 | Adjust pH to 6.0 |
| Purified Water | QS 100% | QS 100% | QS 100% | QS 100% | QS 100% |

-continued

| Example | F | G | H | I | J |
|---|---|---|---|---|---|
| FID | 106039 | 106755 | 107038 | 107039 | 107099 |
| Lot Number | 04-36405 | 04-36173 | 04-36479 | 04-36476 | 04-36632 |
| Osmolality | — | 279 | 204 | 288 | 291 |
| Monovalent cation (Na) conc. needed to adjust pH of buffering anions | 19 mM | 19 mM | 19 mM | 19 mM | 19 mM |

| Microorganism | Log Order Reductions | | | | |
|---|---|---|---|---|---|
| *S. aureus* | | | | | |
| 7 D | 2.1 | 2.2 | 1.7 | 3.4 | 4.4 |
| 14 D | 3.7 | 4.4 | 4.0 | 3.7 | 5.1 |
| 28 D | 5.0 | 5.2 | 5.0 | 5.0 | 5.1 |
| *P. aeruginosa* | | | | | |
| 7 D | 2.6 | 3.2 | 3.0 | 3.4 | 4.9 |
| 14 D | 4.6 | 5.1 | 4.7 | 4.6 | 4.9 |
| 28 D | 5.0 | 5.1 | 5.0 | 5.0 | 4.9 |
| *E. coli* | | | | | |
| 7 D | 1.7 | 1.7 | 1.4 | 1.5 | 3.4 |
| 14 D | 2.3 | 2.8 | 3.0 | 2.3 | 4.9 |
| 28 D | 5.1 | 5.2 | 5.1 | 5.1 | 4.9 |
| *C. albican* | | | | | |
| 7 D | 0.2 | 0.3 | 0.2 | 0.2 | 0.7 |
| 14 D | 0.1 | 0.4 | 0.2 | 0.9 | 1.0 |
| 28 D | 0.4 | 0.7 | 0.6 | 1.3 | 1.2 |
| *A. niger* | | | | | |
| 7 D | 3.0 | 2.7 | 3.0 | 3.0 | 3.4 |
| 14 D | 3.1 | 3.6 | 3.7 | 3.0 | 3.6 |
| 28 D | 3.7 | 4.3 | 3.8 | 3.8 | 3.6 |

EXAMPLES K THROUGH N

In these examples, the amount of sorbitol was reduced to 0.25%, while keeping the boric acid concentration at 1%, in order to reduce the concentration of buffering anionic species. In addition, the compositions of Examples L-N contain 0.75% propylene glycol. The formulations of Examples K and L have an anionic buffer concentration of about 4 mM, which is within the preferred range of less than 5 mM specified herein. The antimicrobial activity of these compositions against *E. coli* at a zinc concentration of 0.18 mM (0.0025 w/v %) is significantly improved, relative to the activity of the formulations in Examples F-J, and the compositions meet USP preservation criteria. In examples M and N, the pH was adjusted to 5.5 and 6.5, respectively, while maintaining the USP preservation efficacy. The results obtained with the formulations of Examples K through N, which are representative of the compositions of the present invention, further demonstrate the importance of limiting the concentration of buffering anions, relative to satisfying preservative efficacy requirements.

| Example | K | L | M | N |
|---|---|---|---|---|
| FID | 107046 | 107047 | 109032 | 109033 |
| Lot Number | 04-36523 | 37157-3 | 05-40452 | 05-40453 |
| Ingredient | | | | |
| Travoprost | 0.004 | 0.004 | 0.004 | 0.004 |
| Polyoxyl 40 Hydrogenated Castor Oil (HCO-40) | 0.5 | 0.5 | 0.5 | 0.5 |
| Zinc Chloride | 0.0025 | 0.0025 | 0.0025 | 0.0025 |
| Boric Acid | 1 | 1 | 1 | 1 |
| Sorbitol | 0.25 | 0.25 | 0.25 | 0.25 |
| Propylene Glycol | None | 0.75 | 0.75 | 0.75 |
| Sodium Hydroxide, and/or Hydrochloric Acid | Adjust pH to 6.0 | Adjust pH to 6.0 | Adjust pH to 5.5 | Adjust pH to 6.5 |
| Purified Water | QS 100% | QS 100% | QS 100% | QS 100% |
| Osmolality | 176 | 272 | 283 | 278 |
| Monovalent cation (Na) conc. needed to adjust pH of buffering anions | 3.9 mM | 4.1 mM | 2 mM | 7.5 mM |

| Microorganism | Log Order Reductions | | | |
|---|---|---|---|---|
| *S. aureus* | | | | |
| 7 D | 2.6 | 4.1 | 3.2 | 3.4 |
| 14 D | 4.7 | 5.0 | 4.8 | 4.8 |
| 28 D | 5.0 | 5.0 | 4.8 | 4.8 |
| *P. aeruginosa* | | | | |
| 7 D | 4.6 | 4.5 | 4.9 | 4.9 |
| 14 D | 5.0 | 5.0 | 4.9 | 4.9 |
| 28 D | 5.0 | 5.0 | 4.9 | 4.9 |
| *E. coli* | | | | |
| 7 D | 2.7 | 1.9 | 3.4 | 3.4 |
| 14 D | 5.1 | 5.0 | 4.9 | 4.9 |
| 28 D | 5.1 | 5.0 | 4.9 | 4.9 |

-continued

| Example | K | L | M | N |
|---|---|---|---|---|
| FID | 107046 | 107047 | 109032 | 109033 |
| Lot Number | 04-36523 | 37157-3 | 05-40452 | 05-40453 |
| *C. albican* | | | | |
| 7 D | 0.1 | 0.2 | 0.1 | 0.2 |
| 14 D | 0.1 | 0.6 | 0.3 | 0.4 |
| 28 D | 0.4 | 1.0 | 0.9 | 1.3 |
| *A. niger* | | | | |
| 7 D | 2.2 | 2.3 | 2.7 | 2.6 |
| 14 D | 2.3 | 3.8 | 3.1 | 2.6 |
| 28 D | 3.0 | 3.5 | 3.8 | 2.8 |

EXAMPLES O AND P

In these examples, the amount of boric acid was reduced. The formulations meet USP preservation criteria and are representative of the compositions of the present invention.

| Example | O | P |
|---|---|---|
| FID | 107519 | 107520 |
| Lot Number | 04-37442 | 04-37443 |
| Ingredient | Concentration (w/v %) | |
| Travoprost | 0.004 | 0.004 |
| Polyoxyl 40 Hydrogenated Castor Oil (HCO-40) | 0.5 | 0.5 |
| Zinc Chloride | 0.0025 | 0.0025 |
| Boric Acid | 0.3 | 0.15 |
| Sorbitol | 0.25 | 0.125 |
| Propylene Glycol | 1.6 | 1.6 |
| Sodium Hydroxide, and/or Hydrochloric Acid | Adjust pH to 6.0 | Adjust pH to 6.0 |
| Purified Water | QS 100% | QS 100% |
| Osmolality | 281 | 247 |
| Sodium Hydroxide conc. | 2.2 mM | 0.5 mM |
| Monovalent cation (Na) conc. needed to adjust pH of buffering anions | 2.2 mM | 0.5 mM |
| Microorganism | Log Order Reductions | |
| *S. aureus* | | |
| 7 D | 4.9 | 5.0 |
| 14 D | 4.9 | 5.0 |
| 28 D | 4.9 | 5.0 |
| *P. aeruginosa* | | |
| 7 D | 5.0 | 5.0 |
| 14 D | 5.0 | 5.0 |
| 28 D | 5.0 | 5.0 |
| *E. coli* | | |
| 7 D | 5.1 | 5.1 |
| 14 D | 5.1 | 5.1 |
| 28 D | 5.1 | 5.1 |
| *C. albican* | | |
| 7 D | 0.3 | 0.2 |
| 14 D | 0.9 | 1.0 |
| 28 D | 1.5 | 2.0 |
| *A. niger* | | |
| 7 D | 2.6 | 2.6 |
| 14 D | 3.0 | 2.3 |
| 28 D | 3.7 | 2.6 |

EXAMPLES Q AND R

The preservation of formulations containing 0.18 mM zinc (0.0025% zinc chloride), with or without boric acid. was evaluated. The results show that antimicrobial activity was greater with the presence of boric acid/polyols. However, the formulation of Example R exhibited sufficient activity to satisfy USP preservative efficacy requirements, even though it did not contain boric acid. The ability of the formulation of Example R to meet preservative efficacy requirements is believed to be attributable in part to the fact that the formulation: (i) did not contain any multivalent anionic buffering agents and (ii) contained a non-ionic agent (i.e., propylene glycol) as the principal osmolality adjusting agent. The formulations of Examples Q and R are representative of the compositions of the present invention.

| Examples | Q | R |
|---|---|---|
| FID | 112306 | 112308 |
| Lot Number | 07-47316 | 07-47318 |
| Ingredients | Concentration (w/v %) | |
| Zinc Chloride | 0.0025 | 0.0025 |
| Tromethamine | None | 0.13 |
| Propylene Glycol | 1.6 | 1.6 |
| Boric Acid | 0.25 | None |
| Mannitol | 0.1 | None |
| Sodium Hydroxide, and/or Hydrochloric Acid | Adjust pH to 7.5 | Adjust pH to 7.5 |
| Purified Water | QS 100% | QS 100% |
| Osmolality (mOsm/kg) | 261 | 232 |
| Sodium Hydroxide concentration | 4.4 mM NaOH | None |
| Monovalent Cation (sodium) needed to adjust pH of buffering anions | 4.4 mM NaOH | * |
| Microorganism | Log Order Reductions | |
| *S. Aureus* | | |
| 6 Hours | 0.5 | 1.4 |
| 24 Hours | 2.6 | 3.5 |
| 7 Days | 5.1 | 5.1 |
| 14 Days | NT | NT |
| 28 Days | NT | NT |
| *Pseudomonas A* | | |
| 6 Hours | 1.4 | 2.8 |
| 24 Hours | 4.0 | 3.8 |
| 7 Days | 5.1 | 5.1 |
| 14 Days | NT | NT |
| 28 Days. | NT | NT |
| *E. Coli* | | |
| 6 Hours | 0.8 | 0.7 |
| 24 Hours | 1.5 | 1.7 |
| 7 Days | 5.1 | 5.1 |
| 14 Days | NT | NT |
| 28 Days. | NT | NT |
| *Candida A.* | | |
| 7 Days | 0.9 | 0.3 |
| 14 Days | NT | NT |
| 28 Days. | NT | NT |
| *A. Niger* | | |
| 7 Days | 1.7 | 0.4 |
| 14 Days | NT | NT |
| 28 Days. | NT | NT |

* This formulation does not contain any buffering anion. However, it contains a buffering cation, tromethamine. pH is adjusted using 8.8 mM HCl.
NT = Not Tested

EXAMPLES Q AND S

A comparison of the formulations of Examples Q and S demonstrates that the preservation efficacy of formulations containing 0.18 mM zinc (0.0025% zinc chloride) is reduced in the presence of low levels of a multivalent metal cation, i.e., calcium. However, the amount of multivalent metal cation in the formulation of Example S (i.e., 2.3 mM), which is less than the upper limit specified herein (i.e., less than 5 mM), was not great enough to significantly inhibit the preservative efficacy of the formulation. The formulations of Examples Q and S are representative of the compositions of the present invention.

| Examples | Q | S |
|---|---|---|
| FID | 112306 | 112307 |
| Lot Number | 07-47316 | 07-47317 |
| Ingredients | Concentration (w/v %) | |
| Zinc Chloride | 0.0025 | 0.0025 |
| Calcium Chloride | None | 0.025 |
| Propylene Glycol | 1.6 | 1.6 |
| Boric Acid | 0.25 | 0.25 |
| Mannitol | 0.1 | 0.1 |
| Sodium Hydroxide, and/or Hydrochloric Acid | Adjust pH to 7.5 | Adjust pH to 7.5 |
| Purified Water | QS 100% | QS 100% |
| Osmolality (mOsm/kg) | 261 | 264 |
| Sodium Hydroxide Conc. | 4.4 mM | 4.5 mM |
| Monovalent Cation (Sodium) needed to adjust pH of buffering anions | 4.4 mM | 4.5 mM |
| Microorganism | Log Order Reductions | |
| *S. Aureus* | | |
| 6 Hours | 0.5 | 0.2 |
| 24 Hours | 2.6 | 1.2 |
| 7 Days | 5.1 | 5.1 |
| 14 Days | NT | NT |
| 28 Days | NT | NT |
| *Pseudomonas A* | | |
| 6 Hours | 1.4 | 0.6 |
| 24 Hours | 4.0 | 0.8 |
| 7 Days | 5.1 | 5.1 |
| 14 Days | NT | NT |
| 28 Days. | NT | NT |
| *E. Coli* | | |
| 6 Hours | 0.8 | 0.6 |
| 24 Hours | 1.5 | 0.7 |
| 7 Days | 5.1 | 5.1 |
| 14 Days | NT | NT |
| 28 Days. | NT | NT |
| *Candida A.* | | |
| 7 Days | 0.9 | 0.6 |
| 14 Days | NT | NT |
| 28 Days. | NT | NT |
| *A. Niger* | | |
| 7 Days | 1.7 | 1.4 |
| 14 Days | NT | NT |
| 28 Days. | NT | NT |

NT = Not Tested

EXAMPLES Q, T AND U

A comparison of the results obtained with the formulations of Examples Q, T and U demonstrates that preservation efficacy improves as the zinc chloride concentration is increased from 0.18 mM zinc (0.0025% zinc chloride) to 1.8 mM zinc (0.025% zinc chloride). All three formulations satisfied USP preservative efficacy requirements. However, the formulation of Example Q (0.18 mM zinc) did not clearly satisfy the Ph. Eur. B. requirements. The formulations of Examples T and U (0.88 and 1.8 mM of zinc, respectively) did clearly satisfy the Ph. Eur. B requirements; however, the use of higher concentrations of zinc (i.e., 1.8 mM in Example U) is not desirable, as such concentrations may product an astringent affect when applied to the eye. The zinc concentration utilized in the formulation of Example U is outside the range specified herein (i.e., 0.04 to 0.9 mM). Consequently, the formulations of Examples Q and T are representative of the compositions of the present invention, while the formulation of Example U is comparative.

| Examples | Q | T | U |
|---|---|---|---|
| FID | 112306 | 112294 | 112148 |
| Lot Number | 07-47316 | 07-47278 | 07-46931 |
| Ingredients | Concentration (w/v %) | | |
| Zinc Chloride | 0.0025 | 0.012 | 0.025 |
| Propylene Glycol | 1.6 | 1.6 | 1.6 |
| Boric Acid | 0.25 | 0.25 | 0.25 |
| Mannitol | 0.1 | 0.1 | 0.1 |
| Sodium Hydroxide, and/or Hydrochloric Acid | Adjust pH to 7.5 | Adjust pH to 7.5 | Adjust pH to 7.5 |
| Purified Water | QS 100% | QS 100% | QS 100% |
| Osmolality (mOsm/kg) | 261 | 261 | 265 |
| Sodium Hydroxide Conc. | 4.4 mM | 4.4 mM | 4.6 mM |
| Monovalent Cation (Sodium) needed to adjust pH of buffering anions | 4.4 mM | 4.4 mM | 4.6 mM |
| Microorganism | Log Order Reductions | | |
| *S. Aureus* | | | |
| 6 Hours | 0.5 | 1.2 | 2.6 |
| 24 Hours | 2.6 | 3.5 | 4.3 |
| 7 Days | 5.1 | 5.0 | 5.0 |
| 14 Days | NT | NT | NT |
| 28 Days | NT | NT | NT |
| *Pseudomonas A* | | | |
| 6 Hours | 1.4 | 1.3 | 2.7 |
| 24 Hours | 4.0 | 3.3 | 4.5 |
| 7 Days | 5.1 | 4.9 | 5.0 |
| 14 Days | NT | NT | NT |
| 28 Days. | NT | NT | NT |
| *E. Coli* | | | |
| 6 Hours | 0.8 | 0.8 | 1.0 |
| 24 Hours | 1.5 | 1.6 | 1.8 |
| 7 Days | 5.1 | 5.0 | 5.0 |
| 14 Days | NT | NT | NT |
| 28 Days. | NT | NT | NT |
| *Candida A.* | | | |
| 7 Days | 0.9 | 2.8 | 5.0 |
| 14 Days | NT | NT | NT |
| 28 Days. | NT | NT | NT |
| *A. Niger* | | | |
| 7 Days | 1.7 | 1.3 | 1.6 |
| 14 Days | NT | NT | NT |
| 28 Days | NT | NT | NT |

NT = Not Tested

EXAMPLES U, V AND W

A comparison of the results obtained with the formulations of Examples U, V and W demonstrates the effect of pH on the antimicrobial activity of the zinc-based preservative systems of the present invention. Specifically, even at a high zinc concentration (i.e., 1.8 mM), the formulation of Example V (pH 5.5) did not satisfy the Ph. Eur. B. preservative efficacy requirements, but the same formulation did satisfy those requirements when the pH was increased to 6.5 (Example W) or 7.5 (Example U). These results demonstrate the preference for use of a slightly alkaline pH in the compositions of the present invention, as specified above. This preference is of even greater importance when concentrations of zinc lower than 1.8 mM are utilized, as in the compositions of the present invention.

| Examples | V | W | U |
|---|---|---|---|
| FID | 112286 | 112287 | 112148 |
| Lot Number | 07-47249 | 07-47632 | 07-46931 |
| Ingredients | Concentration (w/v %) | | |
| Zinc Chloride | 0.025 | 0.025 | 0.025 |
| Propylene Glycol | 1.6 | 1.6 | 1.6 |
| Boric Acid | 0.25 | 0.25 | 0.25 |
| Mannitol | 0.1 | 0.1 | 0.1 |
| Sodium Hydroxide, and/or Hydrochloric Acid | Adjust pH to 5.5 | Adjust pH to 6.5 | Adjust pH to 7.5 |
| Purified Water | QS 100% | QS 100% | QS 100% |
| Osmolality (mOsm/kg) | 263 | 265 | 265 |
| Sodium Hydroxide Conc. | 0.1 mM | 1.0 mM | 4.6 mM |
| Monovalent Cation (Sodium) needed to adjust pH of buffering anions | 0.1 mM | 1.0 mM | 4.6 mM |
| Microorganism | Log Order Reductions | | |
| *S. Aureus* | | | |
| 6 Hours | 0.1 | 0.2 | 2.6 |
| 24 Hours | 0.2 | 2.3 | 4.3 |
| 7 Days | 4.2 | 5.0 | 5.0 |
| 14 Days | NT | NT | NT |
| 28 Days | NT | NT | NT |
| *Pseudomonas A* | | | |
| 6 Hours | 1.2 | 1.4 | 2.7 |
| 24 Hours | 2.1 | 3.2 | 4.5 |
| 7 Days | 4.9 | 4.9 | 5.0 |
| 14 Days | NT | NT | NT |
| 28 Days. | NT | NT | NT |
| *E. Coli* | | | |
| 6 Hours | 0.4 | 0.5 | 1.0 |
| 24 Hours | 0.9 | 1.3 | 1.8 |
| 7 Days | 2.2 | 5.0 | 5.0 |
| 14 Days | NT | NT | NT |
| 28 Days. | NT | NT | NT |
| *Candida A.* | | | |
| 7 Days | 1.0 | 2.0 | 5.0 |
| 14 Days | NT | NT | NT |
| 28 Days. | NT | NT | NT |
| *A. Niger* | | | |
| 7 Days | 2.3 | 2.0 | 1.6 |
| 14 Days | NT | NT | NT |
| 28 Days. | NT | NT | NT |

NT = Not Tested

EXAMPLE X

The formulation of Example X, which is representative of the compositions of the present invention, contained zinc at a concentration of 0.29 mM, had an alkaline pH and satisfied the USP and Ph. Eur. B. preservative efficacy requirements. These results further demonstrate the basis for the above-specified preference for the use of a slightly alkaline pH in the compositions of the present invention.

| Example | X |
|---|---|
| FID | 112736 |
| Lot Number | 07-48252 |
| Ingredients | Concentration (w/v %) |
| Zinc Chloride | 0.004 |
| Propylene Glycol | 1.7 |
| Boric Acid | 0.25 |
| Tromethamine, and/or HCl | Adjust pH to 8.0 |
| Purified Water | QS 100% |
| Osmolality (mOsm/kg) | 265 |
| Tromethamine concentration mM | 12.4 |
| Monovalent Cation (Tromethamine) Needed to adjust pH of buffering anions* | 8.2 |
| Microorganism | Log Order Reductions |
| *S. Aureus* | |
| 6 Hours | 1.9 |
| 24 Hours | 3.9 |
| 7 Days | 4.9 |
| 14 Days | 4.9 |
| 28 Days | 4.9 |
| *Pseudomonas A* | |
| 6 Hours | 2.2 |
| 24 Hours | 3.0 |
| 7 Days | 4.7 |
| 14 Days | 4.7 |
| 28 Days. | 4.7 |
| *E. Coli* | |
| 6 Hours | 0.8 |
| 24 Hours | 1.5 |
| 7 Days | 3.9 |
| 14 Days | 5.0 |
| 28 Days. | 5.0 |
| *Candida A.* | |
| 7 Days | 2.1 |
| 14 Days | 2.9 |
| 28 Days. | 4.1 |
| *A. Niger* | |
| 7 Days | 0.9 |
| 14 Days | 1.9 |
| 28 Days. | 1.8 |

*Calculated using pKa of 8.3

EXAMPLE Y

12-Hydroxystearic acid (HSA) is an impurity and potential degradation product of the excipient polyoxyl 40 hydrogenated castor oil ("HCO-40"). Above a threshold concentration of HSA, zinc ions interact with HSA to form zinc di-12-hydroxystearate particles. This particulate matter formation is not acceptable for an ophthalmic solution. A study was conducted to assess the effect of pH on particulate matter formation in freshly prepared samples of the composition shown in Table Y-1 below. The potential for particulate formation was evaluated by adding varying amounts of HCO-40 to the composition. The results presented in Table Y-2 below show that as pH is decreased, a higher level of HSA is required to form particles. Thus, a lower pH is preferred for a composition containing the surfactant HCO-40 and zinc ions, so that the composition remains free from particulate matter formation throughout its shelf-life. The preferred pH range for such compositions is 5.0 to 6.0. The most preferred pH range for such compositions is 5.5 to 5.9.

TABLE Y-1

Composition of used for the study effect of pH on zinc di-12-hydroxystearate particulate matter formation[a]

| Component | Concentration W/V % |
|---|---|
| Travoprost | 0.004% |
| Polyoxyl 40 Hydrogenated Castor Oil (HCO-40) | 0.5% |
| Boric Acid | 1.0% |
| Zinc Chloride | 0.0025% |
| Sorbitol | 0.25% |
| Propylene Glycol | 0.75% |
| Sodium Hydroxide/ Hydrochloric Acid | Adjust pH.[b] |
| Purified Water | q.s. 100% |

[a]These samples were spiked with HSA.

[b]pH was adjusted to pre-determined values between 5.5 to 6.5

TABLE Y-2

Relationship Between pH and Particulate Matter Formation (by Microscopic Observation) in Freshly Prepared Samples of Composition Containing HSA at Room Temperature

| Total Concentration of HSA | pH at which Particulate Matter[a] was not formed | pH at which Particulate Matter[a] was formed |
|---|---|---|
| 5 ppm | 6.00 | 6.10[b] |
| 6.5 ppm | 5.75 | 5.90 |
| 8 ppm | 5.58 | 5.75 |

[a]Based on microscopic observation of white crystalline particles.

[b]Particles observed visually; hence were not checked microscopically.

EXAMPLE Z

The formulation shown below represents a further example of a self-preserved pharmaceutical composition of the present invention.

| Example | Z |
|---|---|
| Ingredients | Conc. (w/v %) |
| Olopatadine Hydrochloride | 0.111 |
| Propylene glycol | 0.3 |
| Boric Acid | 1.0 |
| Sodium Chloride | 0.17 |
| Zinc Chloride | 0.0025 |
| Sodium Hydroxide Hydrochloric Acid | Adjust pH 7.0 |
| Purified Water | QS 100 |

| II. Physical Parameters | |
|---|---|
| Osmolality (mOsm/kg) | 267,268 |
| Monovalent cation (Na) concentration needed to adjust pH of buffering anions | 6.9 mM |

| PET Results | 6 h | 24 h | 7 d | 14 d | 28 d |
|---|---|---|---|---|---|
| S. aureus | 0.0 | 0.2 | 4.4 | 4.9 | 4.9 |
| P. aeruginosa | 0.4 | 1.3 | 3.7 | 4.9 | 4.9 |
| E. coli | 0.7 | 0.8 | 5.0 | 5.0 | 5.0 |
| C. albicans | | | 0.1 | 0.5 | 1.3 |
| A. niger | | | 1.5 | 1.8 | 1.3 |

EXAMPLES AA THROUGH AD

The formulations in Examples AA and AB contain borate/polyol buffers, whereas the formulations in Example AC and AD contain citrate and phosphate buffers, respectively. All formulations contain 0.11 mM zinc (0.0015% zinc chloride). The formulations in Examples AA and AB, which are representative of the compositions of the present invention, satisfied USP preservative efficacy requirements for the microorganisms tested. The formulations in Examples AC and AD failed to satisfy the USP preservative efficacy requirements, relative to all microorganisms tested. The formulations in Examples AC and AD contained multivalent buffering anions (i.e., citrate and phosphate, respectively) at concentrations of greater than 5 mM. These results demonstrate the importance of limiting the concentration of multivalent buffering anions in the compositions of the present invention.

| Example | AA | AB | AC | AD |
|---|---|---|---|---|
| FID | 109997 | 110009 | 110002 | 110013 |
| Lot Number | 05-42424 | 05-42421 | 05-42428 | 05-42432 |
| Ingredient | | | | |
| Polyoxyl 40 Hydrogenated Castor Oil (HCO-40) | 0.5 | 0.5 | 0.5 | 0.5 |
| Zinc Chloride | 0.0015 | 0.0015 | 0.0015 | 0.0015 |
| Boric Acid | 1 | 1 | None | None |
| Propylene Glycol | 0.4 | 0.4 | 0.4 | 0.4 |
| Sodium Chloride | None | 0.2 | None | None |
| Sodium Citrate (Dihydrate) | None | None | 0.215 | None |
| Dibasic Sodium Phosphate (Anhydrous) | None | None | None | 0.156 |
| Sodium Hydroxide, and/or Hydrochloric Acid | Adjust pH to 7.0 | Adjust pH to 7.0 | Adjust pH to 7.0 | Adjust pH to 7.0 |
| Purified Water | QS 100% | QS 100% | QS 100% | QS 100% |
| Osmolality | 210 | 270 | 76 | 85 |
| Monovalent cation (Na) conc. needed to adjust pH of buffering anions | 4.4 mM | 4.7 mM | 20.4 mM* | 15.8 mM* |

-continued

| Example | AA | AB | AC | AD |
|---|---|---|---|---|
| FID | 109997 | 110009 | 110002 | 110013 |
| Lot Number | 05-42424 | 05-42421 | 05-42428 | 05-42432 |
| Microorganism | Log Order Reductions | | | |
| *S. aureus* | | | | |
| 7 D | 4.8 | 4.8 | 0.9 | 0.9 |
| 14 D | 4.8 | 4.8 | 4.8 | 3.5 |
| 28 D | 4.8 | 4.8 | 4.8 | 4.3 |
| *P. aeruginosa* | | | | |
| 7 D | 4.9 | 4.9 | 0.4 | −0.3 |
| 14 D | 4.9 | 4.9 | 0.5 | −0.4 |
| 28 D | 4.9 | 4.9 | 0.3 | −0.2 |
| *E. col* | | | | |
| 7 D | 4.4 | 4.4 | −0.6 | −0.9 |
| 14 D | 4.4 | 4.4 | −0.4 | −0.8 |
| 28 D | 4.4 | 4.4 | −0.3 | −0.5 |
| *C. albican* | | | | |
| 7 D | NT | NT | NT | NT |
| 14 D | NT | NT | NT | NT |
| 28 D | NT | NT | NT | NT |
| *A. niger* | | | | |
| 7 D | NT | NT | NT | NT |
| 14 D | NT | NT | NT | NT |
| 28 D | NT | NT | NT | NT |

*Calculated based on Pka and concentration of buffer used.

We claim:

1. A multi-dose, self-preserved ophthalmic composition, comprising:
   zinc ions at a concentration of 0.04 to 0.4 mM; and
   borate and polyol, the borate being present in the composition at a concentration of 0.1 to 2.0% w/v and the polyol being present in the composition at a concentration of 0.25 to 2.5% w/v, the polyol comprising propylene glycol in the composition at a concentration of 0.25 to 1.25% w/v and sorbitol in the composition at a concentration of 0.05 to 0.5% w/v;
   wherein: (i) the composition has a concentration of anionic species less than 15 mM; and (ii) the composition exhibits sufficient antimicrobial activity to allow the composition to satisfy USP 27 preservative efficacy requirements.

2. A composition according to claim 1, wherein the composition has a concentration of multivalent buffering anions that is less than 5 mM.

3. A composition according to claim 1, wherein: (i) the composition has a concentration of multivalent buffering anions that is less than 5 mM; and (ii) the composition has a concentration of multivalent metal cations other than zinc that is less than 5 mM.

4. A composition according to claim 1 further comprising an effective amount of a therapeutic agent.

5. A composition according to claim 1 further comprising a therapeutic agent selected from the group consisting of bimatoprost, latanoprost, travoprost and unoprostone.

6. A composition according to claim 5 wherein the therapeutic agent comprises travoprost.

7. A composition according to claim 1 further comprising polyoxyl 40 hydrogenated castor oil wherein the composition has a pH from 5.5 to 5.9.

8. A composition according to claim 1 further comprising a non-ionic surfactant.

9. A composition according to claim 1 further comprising:
   an effective amount of a therapeutic agent;
   wherein:
   i. the composition has a concentration of multivalent buffering anions that is less than 5 mM;
   the composition has a concentration of multivalent metal cations other than zinc that is less than 5 mM; and
   iii. the borate is present in the composition at a concentration of 0.5 to 1.2% w/v.

10. A composition according to claim 9 wherein the therapeutic agent is selected from the group consisting of bimatoprost, latanoprost, travoprost and unoprostone.

11. A composition according to claim 9 wherein the therapeutic agent is travoprost.

12. A composition according to claim 11 further comprising polyoxyl 40 hydrogenated castor oil wherein the composition has a pH from 5.5 to 5.9.

13. A composition according to claim 9 wherein the zinc ions are provided by zinc chloride at a concentration of 0.001 to 0.005 w/v%.

14. A composition according to claim 9 wherein the propylene glycol is present in the composition at a concentration of 0.75 w/v%, the borate is boric acid and is present in the composition at a concentration of 1.0 w/v% and the zinc ions are provided by zinc chloride at a concentration of 0.0025 w/v%.

15. A composition according to claim 1 or claim 9 wherein the composition does not contain multivalent buffering anions and does not contain multivalent cations other than zinc.

16. A composition according to claim 1 wherein the concentration of anionic species in the composition is less than 10 mM.

17. A composition according to claim 1 wherein the concentration of anionic species in the composition is less than 5 mM.

18. A composition according to claim 9 wherein the concentration of anionic species in the composition is less than 10 mM.

19. A composition according to claim 9 wherein the concentration of anionic species in the composition is less than 5 MM.

20. A composition according to claim 1 wherein the composition comprises zinc ions at a concentration of 0.1 to 0.4 m.M.

21. A composition according to claim 9 wherein the composition comprises zinc ions at a concentration of 0.1 to 0.4 mM.

22. A multi-dose, self-presened ophthalmic composition, comprising:
    an effective amount of travoprost;
    zinc ions at a concentration of 0.1 to 0.4 mM wherein the zinc ions are provided by zinc chloride;
    borate and polyol, the borate being present as boric acid in the composition at a concentration of 0.5 to 1.2% w/v and the polyol including propylene glycol and sorbitol, the propylene glycol being present in the composition at a concentration of 0.25 to 1.25% w/v and the sorbitol being present n the composition at a concentration of 0.05 to 0.5% w/v; and
    water;
    wherein: (i) the composition has a concentration of anionic species less than 10 mM; (ii) the composition exhibits sufficient antimicrobial activity to allow the composition to satisfy USP 27 preservative efficacy requirements; and (iii) the composition does not contain multivalent buffering anions and does not contain multivalent cations other than zinc.

23. A composition according to claim 22 further comprising polyoxyl 40 hydrogenated castor oil wherein the composition has a pH from 5.5 to 5.9.

24. A composition according to claim 23 wherein the concentration of travoprost in the composition is 0.004% w/v, the concentration of zinc chloride ionized in the composition is 0.0025% w/v, the concentration of boric acid is 1.0% w/v, the concentration of propylene glycol in the composition is 0.75% w/v, the concentration of sorbitol in the composition is 0,25 w/v % and the concentration of non-ionic surfactant in the composition is 0.5 w/v%.

25. A composition according to claim 22 wherein the composition does not contain multivalent buffering anions and does not contain multivalent cations other than zinc.

26. A multi-dose, self-preserved ophthalmic composition, consisting of:
    an effective amount of travoprost;
    zinc ions at a concentration of 0.1 to 0.4 mM wherein the zinc ions are provided by zinc chloride;
    polyoxyl 40 hydrogenated castor oil;
    borate and polyol, the borate being present as boric acid in the composition at a concentration of 0.5 to 1.2% w/v and the polyol including propylene glycol and sorbitol, the propylene glycol being present in the composition at a concentration of 0.25 to 1.25% w/v and the sorbitol being present in the composition at a concentration of 0.05 to 0.5% w/v;
    sodium hydroxide and/or hydrochloric acid to adjust pH; and
    water;
    wherein: (i) the composition has a concentration of anionic species less than 10 mM; (ii) the composition exhibits sufficient antimicrobial activity to allow the composition to satisfy USP 27 preservative efficacy requirements; (iii) the composition does not contain multivalent buffering anions and does not contain multivalent cations other than zinc; and (iv) the composition has a pH from 5.5 to 5.9.

27. A multi-dose, self-preserved ophthalmic composition, consisting of:
    travoprost at a concentration of 0.004% w/v;
    ionized zinc chloride at a concentration of 0.0025% w/v;
    polyoxyl 40 hydrogenated castor oil at a concentration of 0.5% w/v;
    borate and polyol, the borate being present as boric acid in the composition at a concentration of 1.0% w/v and the polyol including propylene glycol and sorbitol, the propylene glycol being present in the composition at a concentration of 0.75% w/v and the sorbitol being present in the composition at a concentration of 0.25 w/v%;
    sodium hydroxide and/or hydrochloric acid to adjust pH; and
    water;
    Wherein: (i) the composition has a concentration of anionic species less than 5 mM; (ii) the e composition exhibits sufficient antimicrobial activity to allow the composition to satisfy USP 27 preservative efficacy requirements; (iii) the composition does not contain multivalent buffering anions and does not contain multivalent cations other than zinc; and (iv) the composition has a pH from 5.5 to 5.9.

28. A multi-dose, self-preserved ophthalmic composition, consisting of:
    travoprost at a concentration of 0.004% w/v;
    zinc chloride ionized in the composition at a concentration of 0.0025% w/v;
    polyoxyl 40 hydrogenated castor oil at a concentration of 0.5% w/v; and
    borate and polyol, the borate being present in the composition as boric acid at a concentration of 1.0% w/v and the polyol including propylene glycol and sorbitol, the propylene glycol being present in the composition at a concentration of 0.75% w/v and the sorbitol being present in the composition at a concentration of 0.25 w/v%;
    sodium hydroxide and/or hydrochloric acid to adjust pH; and
    water;
    wherein: (i) the composition has a concentration of anionic species less than 15 mM; and (ii) the composition exhibits sufficient antimicrobial activity to allow the composition to satisfy USP 27 preservative efficacy requirements.

* * * * *